United States Patent
Andersson et al.

(10) Patent No.: US 10,794,797 B2
(45) Date of Patent: Oct. 6, 2020

(54) DEVICE AND METHOD FOR SAMPLING, PREPARING AND ANALYSING A SAMPLE

(71) Applicant: BTG INSTRUMENTS AB, Säffle (SE)

(72) Inventors: Niclas Andersson, Karlstad (SE); Bengt Anders Skålén, Säffle (SE); Stig Norder, Säffle (SE)

(73) Assignee: BTG INSTRUMENTS AB, Säffle (SE)

( * ) Notice: Subject to any disclaimer, the term of this patent is extended or adjusted under 35 U.S.C. 154(b) by 9 days.

(21) Appl. No.: 14/872,180

(22) Filed: Oct. 1, 2015

(65) Prior Publication Data

US 2016/0025602 A1 Jan. 28, 2016

Related U.S. Application Data

(63) Continuation of application No. PCT/SE2014/050387, filed on Apr. 2, 2014.

(30) Foreign Application Priority Data

Apr. 2, 2013 (SE) ........................................ 1350407

(51) Int. Cl.
| | |
|---|---|
| *G01N 1/38* | (2006.01) |
| *G01N 1/20* | (2006.01) |
| *G01N 1/34* | (2006.01) |
| *G01N 33/34* | (2006.01) |
| *G01N 21/47* | (2006.01) |
| *G01N 21/55* | (2014.01) |
| *G01N 21/59* | (2006.01) |

(Continued)

(52) U.S. Cl.
CPC ............. *G01N 1/2035* (2013.01); *G01N 1/34* (2013.01); *G01N 1/38* (2013.01); *G01N 21/4738* (2013.01); *G01N 21/55* (2013.01); *G01N 21/59* (2013.01); *G01N 33/343* (2013.01); *G01N 2001/1025* (2013.01); *G01N 2001/205* (2013.01); *G01N 2001/4088* (2013.01); *G01N 2201/02* (2013.01)

(58) Field of Classification Search
CPC ........... G01N 1/2035; G01N 1/34; G01N 1/38
USPC ....................................................... 73/61.72
See application file for complete search history.

(56) References Cited

U.S. PATENT DOCUMENTS

| | | |
|---|---|---|
| 5,625,157 A | 4/1997 | Piirainen |
| 5,786,894 A | 7/1998 | Shields et al. |
| 6,018,989 A | 2/2000 | Kubbillum |

(Continued)

FOREIGN PATENT DOCUMENTS

| | | |
|---|---|---|
| DE | 19613985 | 11/1997 |
| EP | 2405251 | 1/2012 |

(Continued)

*Primary Examiner* — John Fitzgerald
*Assistant Examiner* — Rodney T Frank
(74) *Attorney, Agent, or Firm* — Gabriela B. Tomescu, Esq.; Bergenstråhle & Partners AB

(57) ABSTRACT

A device for sampling, preparing and analysing a sample, for example a suspension, comprises: a sampling device adapted to sampling a fluid sample, at least one sample preparation unit adapted to prepare the sample, and at least one analysing unit. By adapting the device for sampling and analysing a sample for placement in direct vicinity to a process pipe and adapting the sampling device to sample a fluid sample directly from a gate, a compact and cost-efficient device is provided, which also provides fast feedback to a process to be controlled.

6 Claims, 2 Drawing Sheets

(51) Int. Cl.
  *G01N 1/40* (2006.01)
  *G01N 1/10* (2006.01)

(56) References Cited

U.S. PATENT DOCUMENTS

| | | | |
|---|---|---|---|
| 2003/0030005 A1 | 2/2003 | Karki et al. | |
| 2005/0005685 A1* | 1/2005 | Weber | B07B 1/02 73/61.71 |
| 2007/0248958 A1* | 10/2007 | Jovanovich | B01F 11/0071 435/6.19 |
| 2008/0250848 A1* | 10/2008 | Karki | G01N 1/38 73/54.01 |

FOREIGN PATENT DOCUMENTS

| | | |
|---|---|---|
| JP | 2004 294174 A | 10/2004 |
| WO | 03046518 | 6/2003 |
| WO | 2006106177 | 10/2006 |

* cited by examiner

DEVICE AND METHOD FOR SAMPLING, PREPARING AND ANALYSING A SAMPLE

This application is a continuation of PCT/SE2014/050387, filed 2 Apr. 2014, which claims priority to Swedish application No. SE-1350407-1 filed 2 Apr. 2013, the entire contents of each of which are hereby incorporated by reference.

TECHNICAL FIELD

The present invention relates generally to device for sampling, preparing and analysing a sample, such as a suspension, preferably a fibre suspension.

BACKGROUND ART

Many industrial processes require different forms of monitoring, analysing and control systems for keeping the consumption of raw material down while providing an optimal and reliable end product. Industrial manufacturing is often at a large scale and is therefore also very energy consuming, which further increases the demand for controlling the process in order to minimize the costs for manufacturing the end product.

Within for example the paper industry the preparation of pulp is monitored at one or more locations along the process line. The process is monitored by regular sampling of the pulp and the condition thereof is determined through different analyses. The collected measurement values are fed back and for example further addition of a raw material or a chemical agent in the process is performed. This keeps unnecessary use of different raw materials, chemical agents, water and energy down while keeping costs down and provides an even quality of the product.

Certain systems which are used today for optimization of process control are made up of several modules and measuring tools. Systems for automated sampling of for example pulp comprising several modules are used today, but these are not suitable for arrangement on a pipe. Usually, the modules are not provided adjacent to the monitored process, for example a pipe with a fibre suspension. Instead, the suspension is transported in long pipes or hoses to the system.

A drawback with prior art systems for sampling, preparing and analysing a sample is that they are costly and bulky. Also, the procedure for sampling a sample may be too complicated if just a single sample is to be sampled or if the process needs to be sampled in a single position only.

Since analysing devices are expensive it is known to connect several measuring locations with separate sampling devices to one single central preparation and analysing device or module. The measuring and analysing frequency for each measuring location is therefore relatively low and there is also a delay between the sampling of a sample and the analysing thereof, resulting in a delayed control feedback.

SUMMARY OF INVENTION

An object of the present invention is to provide a device for sampling, preparing and analysing a sample, such as a suspension, which removes or at least mitigates the problems of prior art systems and which provides an improved process control.

According to the invention, there is provided a device for sampling, preparing and analysing a sample, for example a suspension, comprising: a sampling device adapted to sampling a fluid sample, at least one sample preparation unit adapted to prepare the sample, and at least one analyser, which is characterized in that the device for sampling and analysing a sample is adapted to be placed in direct vicinity to a process pipe and the sampling device is adapted to sample a fluid sample directly from a gate. The sampling device is preferably adapted to bring the fluid sample directly to the preparation unit.

By providing a device which is placed in direct vicinity to a process pipe, several advantages are obtained. By removing a long pipe or hose for transportation of the sample, a small and compact device is provided. This also gives shorter time to the analysing unit, resulting in faster feedback to the process to be controlled.

In a preferred embodiment, the device for sampling, preparing and analysing a sample comprises a first and a second sample preparation unit interconnected by means of a pipe, wherein the first sample preparation unit comprises a first chamber and a first screen and the second sample preparation unit comprises a second chamber and a second screen. The first and second chambers and their interconnection are preferably configured so that no part of a fluid sample can be moved from the first to the second chamber by means of gravity only.

In a preferred embodiment, the first sample preparation unit comprises a coarse screen in the upper portion of the first chamber.

The analysing unit is preferably an optical unit for measuring any of the following: absorbance, reflectance, and fluorescence, preferably an optical unit adapted to measure both absorbance and reflectance. The analysing unit may also be an image analyser.

According to a second aspect of the invention there is provided a method for sampling, preparing and analysing a sample, preferably a suspension, by means of the inventive device, wherein the method comprises the following steps: sampling a fluid sample by means of a sampling device bringing, by means of the sampling device, the sample to a preparation device adapted to prepare the sample, and analysing the sample, wherein the method is characterized in that the device for sampling and analysing a sample is adapted to be placed in direct vicinity to a process pipe, whereby the sample is transported by the sampling device directly to the preparation unit, and the sampling device is adapted to sample a fluid sample directly from a gate.

BRIEF DESCRIPTION OF DRAWINGS

The invention is now described, by way of example, with reference to the accompanying drawings, in which.

DESCRIPTION OF EMBODIMENTS

In the following, a detailed description of a device and a method for sampling, preparing and analysing a sample will be given.

Figure 1:
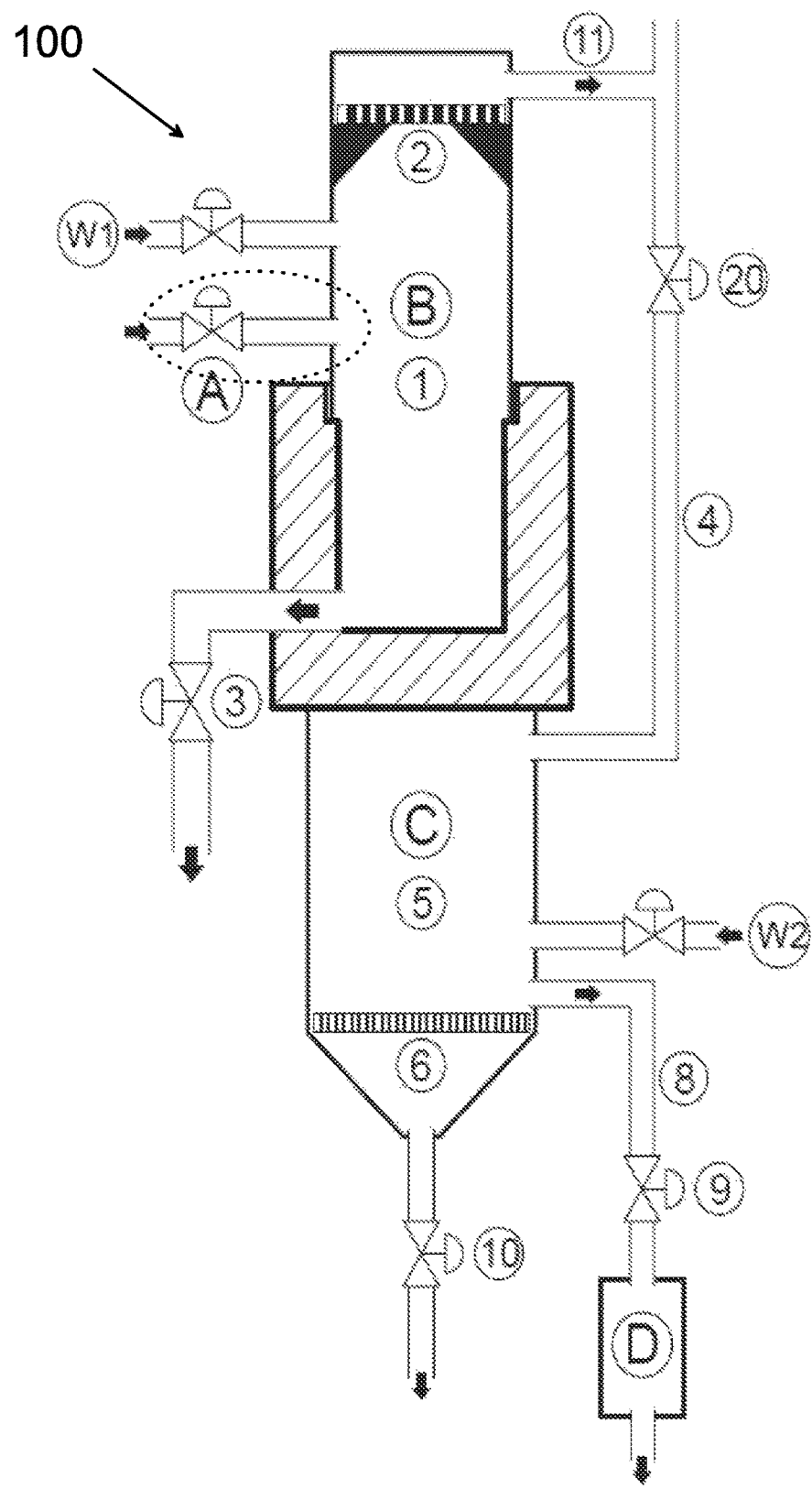
FIG. 1 shows an overall diagram of a device for sampling, preparing and analysing a sample according to the invention.

FIG. 1 shows an overall drawing of a device according to the invention. The device, generally designated 100, is adapted to be placed in direct vicinity to a process pipe (not shown in FIG. 1). The device 100 comprises different units or modules, such as a sampling device A, two sample preparation units B and C and an analysing unit D. Other well-known components, such as nozzles, hoses, valves etc. are not shown or described in detail.

The device is preferably used on washed accept fibres from a pulp suspension but can also be used to treat other samples in order to measure certain parameters in a reject, such as shives, slivers and chips, or a washing filtrate.

Figure 2:
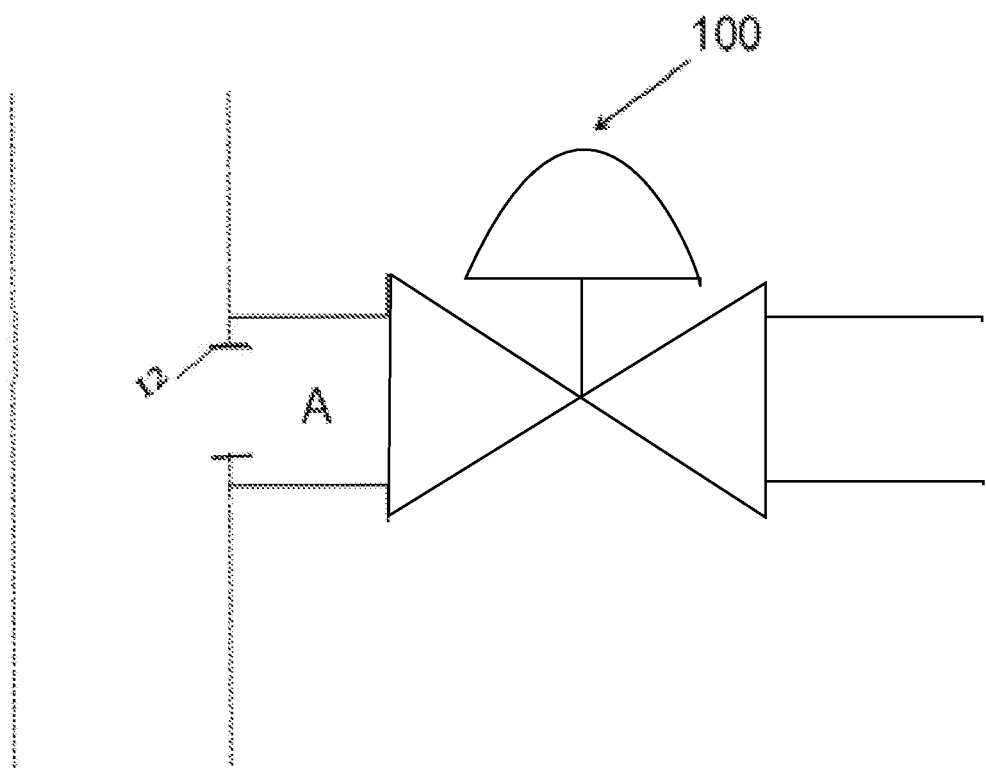
FIG. 2 is a detailed view of part of the device shown in FIG. 1.

The device for sampling, preparing and analysing a sample is adapted to be placed in direct vicinity to a process pipe and the sampling device A is therefore adapted to sample a fluid sample directly from a gate 12. This is shown in more detail in FIG. 2, which is an enlarged view of the area of FIG. 1 which is encircled by a dashed line, i.e., the sampling device A and its connection to a process pipe, shown in dashed lines in the figure. It is also seen that the sampling device is connected directly to the first preparation unit, without any intervening pipe or hose.

The first preparation unit B comprises a first chamber 1 and a first coarse screen 2 provided in the upper portion of the first chamber. The first screen preferably has a filter hole size of about 2 millimetres in diameter. In the lower portion of the chamber 1 an outlet valve 3 for coarse reject is provided.

A water inlet W1 is provided for feeding water to the first chamber 1.

The first and second sample preparation units B, C are interconnected by means of a pipe 4 provided with a valve 20. The second preparation unit C comprises a second preparation chamber and a second finer screen 6 in a lower portion thereof. The second screen 6 preferably has a hole size of less than 1 millimetre in diameter, although the sizes of the holes are adapted to the requirements for the process in question. Below the second screen 6 there is provided an outlet valve 10. The second sample preparation unit C also comprises a second water inlet W2 for washing water.

The second preparation unit C and the analysing unit D are interconnected by means of a pipe 8 with a valve 9.

It is realized that due to the configuration of the first and second preparation units B, C and their interconnection, no part of the sampled suspension sample can be moved from the first to the second chamber by means of gravity only.

A method for sampling, preparing and analysing a sample will now be described in detail. A sample is taken from a process pipe, shown in FIG. 2, by means of the sampling device A. The sample is moved directly into the first preparation unit B. When in the first preparation unit B, the sample is moved by means of water entering through the water inlet W1 and passes the first screen 2, wherein coarse reject is blocked from passing. This coarse reject is flushed out from the first preparation unit B through the outlet valve 3.

The finer fibre material which has been treated and has a size less than the size of the holes in the first screen 2, preferably so called accept fibres, is brought through the first screen 2 by means of the water pressure from the water from the water inlet W1, through the pipe 4 and into the second preparation unit C. The principle of transporting the accept fibres upward through the first screen 2 by means of the flow of water and into a second preparation unit C results in less contamination of the material entering the second preparation unit C. In other words, any leakage through the valve 20, in combination with any leakage through the sampling device A and unwashed rest material in the first chamber 1 cannot directly contaminate the material collected in the second chamber 5.

Water is added in the second chamber 5 and the sample is washed. When the second chamber 5 has been filled as desired, the inflow of washing water is interrupted and is drained through the second fine screen 6 and outlet valve 10. This washing can be repeated several times if required. Left on the second screen 6 are the dewatered fibres. These fibres comprising cellulose fibres making up the measuring material, i.e., accept fibres, are treated by dilution in order to be transported via the pipe 8 to the analysing unit D for analysing.

The valve 9 in the pipe 8 is opened to allow the sample to pass to the analysing unit D, such as a measuring cell. The analysing unit D can be any measuring unit, such as an optical unit for measuring absorbance, reflectance, fluorescence, or an image analyser. In a preferred embodiment, the analysing unit D is an optical unit adapted to measure both absorbance and reflectance.

The result from the analysing unit can be forwarded and processed by means of a processor, for example. The result can for example be used to influence the process by mechanical or manual feedback in different ways, such as by controlling the amount of water or chemical agents added to the process, the amount of energy etc.

A preferred embodiment of a device and a method for sampling, preparing and analysing a sample has been described. It will be realized that this can be varied within the scope of the appended claims without departing from the inventive idea. Thus, a device with two preparation units has been described. It will be realized that it can comprise just one preparation unit or more than two preparation units, depending on the kind of process and sample etc.

The invention claimed is:

1. A device for sampling, preparing and analysing a sample of a fiber suspension, comprising: —a sampling device adapted to sampling a fiber suspension sample, —at least one analysing unit, a first and a second sample preparation unit adapted to prepare the sample, the first and a second sample preparation units being interconnected by means of a pipe connecting to an upper portion of the first sample preparation unit, wherein the first sample preparation unit comprises a first chamber and a first screen and the second sample preparation unit comprises a second chamber and a second screen, wherein the first chamber is placed above the second chamber and the first and second chambers and their interconnection are configured so that no part of a fiber suspension sample can be moved from the first to the second chamber by means of gravity only and wherein the fiber suspension sample is transported upward through the first screen and into a second preparation unit and wherein the first screen is a coarse screen provided in an upper portion of the first chamber of the first sample preparation unit and the second screen is a fine screen provided in a lower portion of the second chamber of the second sample preparation, wherein the second screen has a hole size that is smaller than a hole size of the first screen, wherein the device for sampling and analysing a sample is adapted to be placed attached to a process pipe and the sampling device is adapted to sample a fiber suspension sample directly from a gate.

2. The device for sampling, preparing and analysing a sample according to claim 1, wherein the sampling device is adapted to bring the fluid sample directly to the preparation unit.

3. The device for sampling, preparing and analysing a sample according to claim 1, wherein the analysing unit is an optical unit for measuring any of the following: absorbance, reflectance, and fluorescence, preferably an optical unit adapted to measure both absorbance and reflectance.

4. The device for sampling, preparing and analysing a sample according to claim 1, wherein the analysing unit is an image analyser.

5. A method for sampling, preparing and analysing a sample of a fiber suspension, by means of a device according to claim 1, comprising the following steps:
   sampling a fiber suspension sample by means of a sampling device,
   bringing, by means of the sampling device, the fiber suspension sample to a preparation device adapted to prepare the fiber suspension sample, and
   analysing the fiber suspension sample,
wherein the device for sampling and analysing a sample is adapted to be placed attached to a process pipe, and
the sampling device is adapted to sample a fiber suspension sample directly from a gate.

6. The method according to claim 5, wherein the fiber suspension sample is brought by the sampling device directly to the preparation unit.

\* \* \* \* \*